(12) United States Patent
Linares et al.

(10) Patent No.: US 9,883,868 B2
(45) Date of Patent: Feb. 6, 2018

(54) TISSUE AND BONE GRAFT REMOVAL DEVICE

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US); Ryan T. Greene, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 778 days.

(21) Appl. No.: 14/454,335

(22) Filed: Aug. 7, 2014

(65) Prior Publication Data

US 2014/0350584 A1 Nov. 27, 2014

Related U.S. Application Data

(62) Division of application No. 13/787,435, filed on Mar. 6, 2013, now Pat. No. 9,095,345.

(60) Provisional application No. 61/607,219, filed on Mar. 6, 2012.

(51) Int. Cl.
| | |
|---|---|
| *A61B 17/16* | (2006.01) |
| *A61B 17/14* | (2006.01) |
| *A61B 17/00* | (2006.01) |
| *A61B 90/30* | (2016.01) |
| *A61B 90/00* | (2016.01) |

(52) U.S. Cl.
CPC ........ *A61B 17/149* (2016.11); *A61B 17/1606* (2013.01); *A61B 17/1659* (2013.01); *A61B 90/37* (2016.02); *A61B 2017/00561* (2013.01); *A61B 2017/00734* (2013.01); *A61B 2090/309* (2016.02)

(58) Field of Classification Search
CPC ............ A61K 2300/00; A61B 17/1671; A61B 7/1611; C12N 2506/03; C12N 2500/32
See application file for complete search history.

(56) References Cited

U.S. PATENT DOCUMENTS

| | | |
|---|---|---|
| 4,722,338 A | 2/1988 | Wright et al. |
| 4,733,663 A | 3/1988 | Farley |
| 4,777,948 A | 10/1988 | Wright |
| 5,026,375 A | 6/1991 | Linovitz et al. |
| 5,061,269 A | 10/1991 | Muller |
| 5,273,519 A | 12/1993 | Koros et al. |
| 5,385,570 A | 1/1995 | Chin et al. |
| 5,451,227 A | 9/1995 | Michaelson |
| 5,582,618 A | 12/1996 | Chin et al. |
| 5,653,713 A | 8/1997 | Michelson |

(Continued)

OTHER PUBLICATIONS

Angled Kerrison Rongeur, www.neurosurvival.ca/computerassistedlearning/surgical_technique_equipment/equipment_Kerrison_Rongeur.htm, dated Feb. 6, 2012, 1 page.

*Primary Examiner* — Sean Dougherty
*Assistant Examiner* — Patrick Fernandes
(74) *Attorney, Agent, or Firm* — Dinsmore & Shohl LLP

(57) ABSTRACT

The present invention discloses a rongeur type bone and cartilage removal device incorporating first and second pivotally secured handles, the first handle terminating at a forward end in a first jaw exhibiting a plurality of extending teeth, with second handle terminating in a second jaw opposing the first jaw and exhibiting a continuous blade edge against which the teeth seats during pivotal motion of the jaws.

3 Claims, 4 Drawing Sheets

(56) References Cited

U.S. PATENT DOCUMENTS

| | | | |
|---|---|---|---|
| 5,782,849 A | 7/1998 | Miller | |
| 5,925,050 A * | 7/1999 | Howard, III | A61B 17/1611 |
| | | | 606/170 |
| 6,015,412 A * | 1/2000 | Mifsud | A61B 17/1608 |
| | | | 606/174 |
| 6,142,997 A | 11/2000 | Michelson | |
| 6,200,320 B1 | 3/2001 | Michelson | |
| 6,221,007 B1 | 4/2001 | Green | |
| 6,575,977 B1 | 6/2003 | Michelson | |
| 6,695,849 B2 | 2/2004 | Michelson | |
| 7,011,663 B2 | 3/2006 | Michelson | |
| 7,297,147 B2 | 11/2007 | Michelson | |
| 7,637,872 B1 | 12/2009 | Fox | |
| 7,922,723 B2 | 4/2011 | Michelson | |
| 8,241,290 B2 | 8/2012 | Michelson | |
| 2002/0049460 A1* | 4/2002 | Mazur | A61B 17/1606 |
| | | | 606/167 |
| 2005/0049520 A1* | 3/2005 | Nakao | A61B 10/06 |
| | | | 600/562 |
| 2007/0213735 A1 | 9/2007 | Saadat et al. | |
| 2010/0179557 A1 | 7/2010 | Husted | |

\* cited by examiner

TISSUE AND BONE GRAFT REMOVAL DEVICE

CROSS-REFERENCE TO RELATED APPLICATIONS

This Application is a Division of application Ser. No. 13/787,435 filed on Mar. 6, 2013. Application Ser. No. 13/787,435 claims the benefit of U.S. Provisional Application 61/607,219 filed on Mar. 6, 2012, the contents of which are incorporated herein in its entirety.

FIELD OF THE INVENTION

The present invention is directed to a bone and tissue removal device, such as is known as a rongeur type instrument (French for rodent or gnawer) which is used for opening a window in a bone for any number of purposes not limited to neurosurgery (skull) or orthopedic (musculoskeletal) surgery, as well as oral maxillofacial, hand or other surgical procedures. The removal device according to the present invention improves upon prior art "rongeur" type instruments and provides a manual pliers type variant with alligator type gnawing teeth incorporated into a first jaw which aligns with an opposing and depth defining collection chamber exhibiting an upper razor edge associated with a second jaw, an ejection mechanism including an elongated and pivotally actuated scoop which is operable to eject previously collected debris from within the collection chamber of the second jaw.

BACKGROUND OF THE INVENTION

Rongeur surgical cutting instruments are known in the art for removing sections of bone or cartilage. Notable examples of these include the surgical rongeurs depicted in each of U.S. Pat. No. 5,653,73 and U.S. Pat. No. 6,142,997 and which disclose two shaft members capable of reciprocating motion relative to each other wherein one shaft member terminates in a foot plate and the other shaft member includes a combined cutting element and disposable storage chamber. The rongeur may be manually activated or solenoid powered by a battery.

A further example of an adjustable powered rongeur is depicted in US 2010/0179557 to Husted and which teaches an adaptable deburring bit and independent nerve sensors that facilitate positioning of the instrument to a proximate surgery site. The medical instrument has a hand piece on a proximal end of a shaft and a hollow tip portion on a distal end of the shaft. The hand piece includes a handgrip and a squeezable trigger portion, whereby the trigger portion is independently compressible of the handgrip. The trigger portion controls a rotatable surgical tool bit which is housed in the tip portion and powered by a connecting drive system. A safety apparatus is provided on the grip portion, capable of locking the instrument and a monitoring system disposed on the tip portion, in order to identify proximity of nerve endings.

SUMMARY OF THE INVENTION

The present invention discloses a rongeur type bone and cartilage removal device incorporating first and second pivotally secured handles, the first handle terminating at a forward end in a first jaw exhibiting a plurality of extending teeth, with second handle terminating in a second jaw opposing the first jaw and exhibiting a continuous blade edge against which the teeth seats during pivotal motion of the jaws in order to successively excise increments of bone for evacuation through the passageway and into the collection chamber. The first and second jaws each exhibit an elongated and depth defining shape, with the first jaw being an upper and downwardly open jaw and the second jaw being a lower and upwardly open jaw.

A pivotally actuated scoop can be associated with the second lower jaw for removing previously stored debris. A finger projection extends from a pivotal washer shaped portion in a direction opposite a forward projecting direction of the scoop, a tab extending from the finger and seating in a first position within an underside of the second handle in engagement with a forward end location of an embedded stem.

Yet additional features include a coil spring seating within the second handle and biasing against the finger. A push button being incorporated into a remote location of the second handle and, upon being depressed, permitting a second coil spring embedded in a rear location of the second handle to cause a linear retraction of the embedded stem resulting in release of the tab and subsequent upward pivoting of the scoop.

BRIEF DESCRIPTION OF THE DRAWINGS

Reference will now be made to the attached drawings, when read in combination with the following detailed description, wherein like reference numerals refer to like parts throughout the several views, and in which:

FIG. 4 is a similar view to that shown in FIG. 3 and illustrating the selected trigger mechanism incorporating handle and integrally extending jaw in lengthwise cutaway in order to better depict inner working mechanism operable upon depressing the handle located button for pivotally actuating the coaxially supported and elongated scoop from within the collection chamber interior of the jaw for ejecting previously collected debris from.

DETAILED DESCRIPTION OF THE PREFERRED EMBODIMENTS

Figure 1:
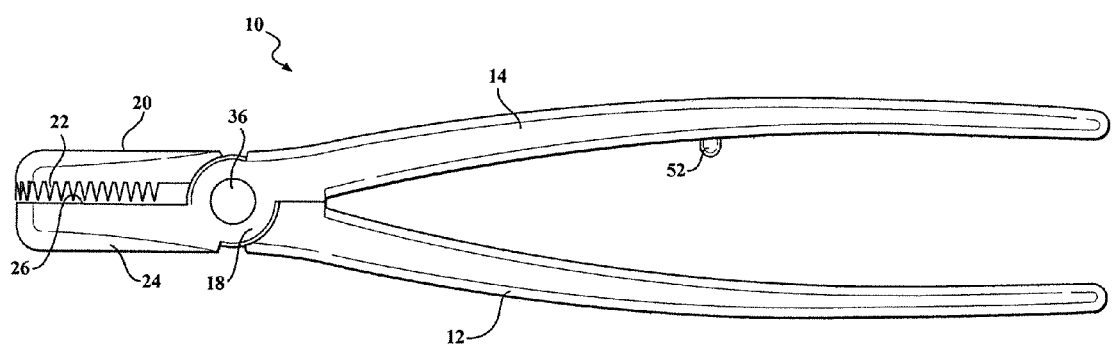
FIG. 1 is a side view of a manual pliers type variant is also disclosed with alligator type gnawing teeth incorporated into a first jaw which aligns with an opposing and depth defining collection chamber exhibiting an upper razor edge associated with a second jaw.

Referring further to FIGS. 1-4, a series of side, perspective and cutaway views are generally shown at 10 of a manual pliers type variant of tissue and bone graft removal device according to the present invention. The pliers type rongeur device incises or removes a small volume of bone or the like with each iteration or bite and includes a first handle 12 and a second handle 14.

Each of the handles 12 and 14 are contoured along their rear extending grasping portions and each includes a circular overlapping and pivotally joined portions 16 (best shown in FIGS. 2-3) and 18 (shown in each of FIGS. 1-3), respectively. The first handle 12 terminates forwardly of its pivotally overlapping portion 16 in an integrally formed upper jaw 20 exhibiting an elongated depth defining and downwardly open profile integrating a continuous plurality of alligator type gnawing teeth 22.

The second handle 14 likewise terminates forwardly of its pivotally overlapping portion 18 in a like integrally formed and upwardly open facing and depth defining lower jaw 24 which exhibits a substantially identically configured contour as the upper jaw 20. The lower jaw 24 exhibits an upper continuous blade edge 26 and which matches the profile of the downwardly facing teeth 22 so that that, upon positioning the jaws 20 and 24 on opposite sides of a section of bone to be removed, inward opposing compression applied to the handles results in the jaws pivoting together and the teeth 22 to abut the opposite continuous razor or blade edge 26 concurrent with a volume of bone or like debris being excised or "bitten off" and deposited within an interior chamber 28 (see FIGS. 2 and 4) defined in the lower jaw 24.

Figure 2:
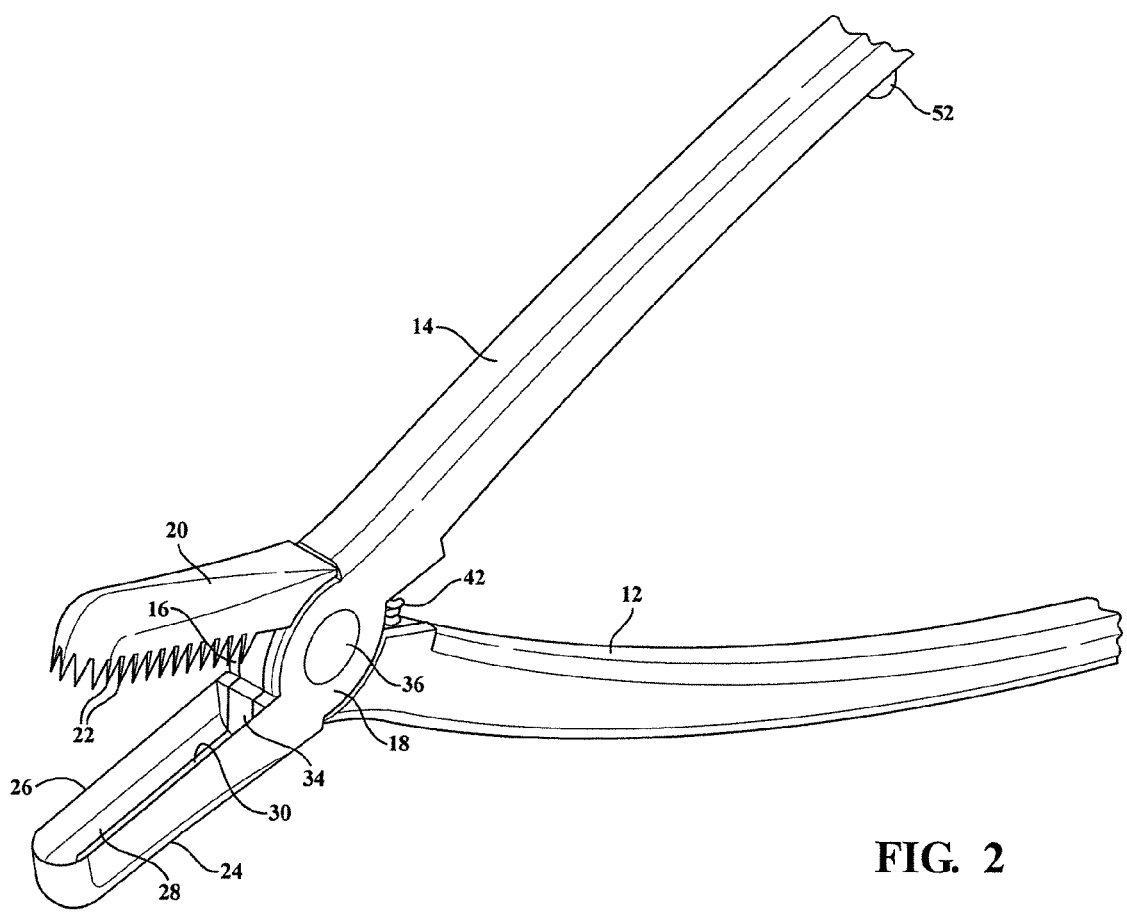
FIG. 2 is a rotated perspective of the manual pliers type variant of FIG. 1 and which better depicts the pivotally opposing and incising nature of the upper alligator teeth and opposing elongated collection chamber with upper facing and continuous razor edge.
Figure 3:
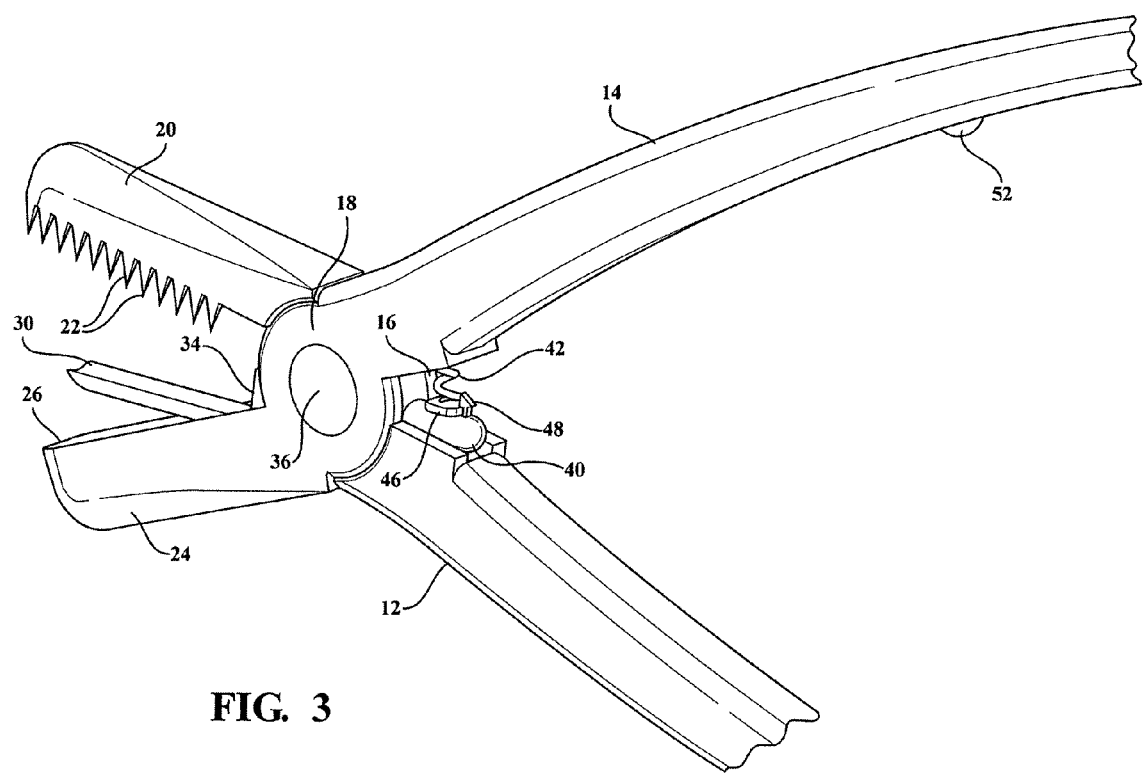
FIG. 3 is a rotated rear facing view of the pliers type variant of FIG. 1 and better illustrating an external depiction of a trigger ejection mechanism for removing debris from the collection chamber via a pivotally actuated scoop.
Figure 4:
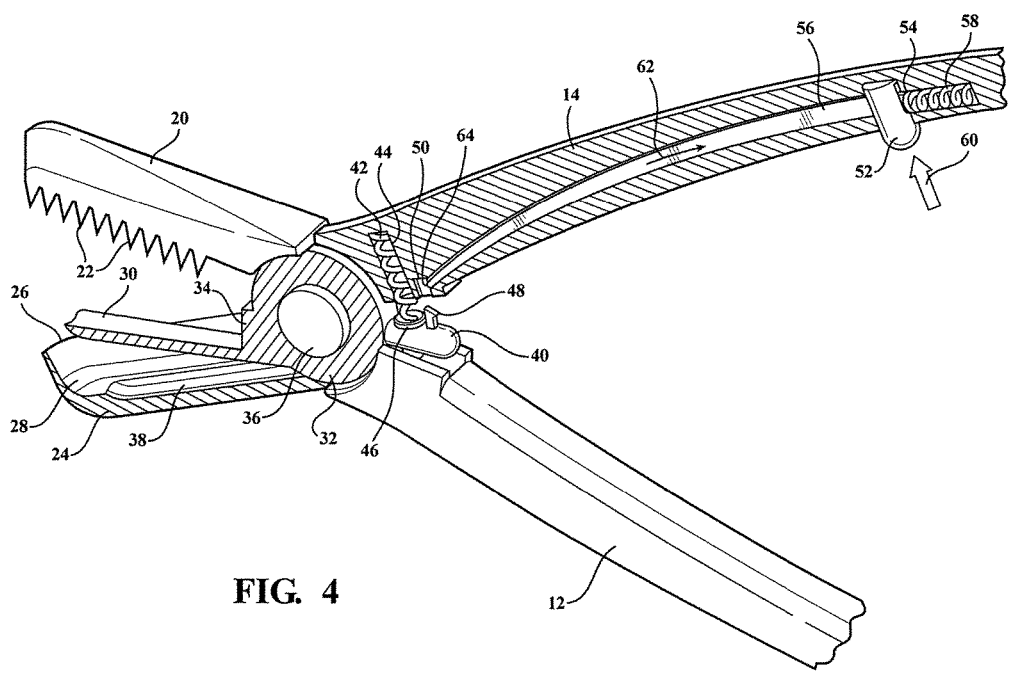

With reference to FIGS. 2-4, additionally illustrated is a trigger ejection mechanism for assisting in easy ejection of previously deposited bone and like debris from within the lower jaw collection chamber 28. The ejection mechanism includes an elongated scoop 30 extending from a pivotally supported washer shaped portion 32 (see as best shown in FIG. 4 and in which the scoop 30 is connected to the washer portion 32 via a stepped location 34) which is mounted upon a coaxial pin or hub 36 extending through an aligning aperture associated with at least one of the overlapping portions 16 or (as shown in FIG. 2) 18 so that the elongated scoop 30 (exhibiting an arcuate profile in cross section) pivots from a first recessed seating location (FIG. 2) in which the scoop seats within a recessed matching base inner profile 38 (FIG. 4) to a second upwardly pivoted location (FIGS. 3 and 4) in which the scoop 30 upwardly ejects the debris from within the chamber.

As again best shown in FIG. 4, additional features incorporated into the trigger ejection mechanism include an integral rearwardly projecting finger 40 extending from the coaxially supported washer shaped 32. A coil spring 42 seats within an inner elongated and recessed profile, at 44, defined in depth extending fashion from an underside accessible location of the second handle 14 proximate the overlapping portions 16/18 of the jaws 12/14, with a base mounting location 46 of the spring 42 engaging the finger projection 40 at an offset location from its pivot fulcrum provided by the coaxial mounting hub 36.

A tab 48 extends upwardly from a rearward proximate end of the finger 40 rearwardly of the coil spring 42 and seats within a mating recess profile 50 defined in a rearwardly spaced and downwardly communicating location of the upper handle 14 which is proximate to the inner seating location of the spring 42 as again shown in FIG. 4. A push button 52 is spring biased at a mounted at a rearward location of the upper handle 14 and exhibits an inner slot 54 through which is received a rearward extending end of an elongated stem 56 embedded within an elongated recess defined in the handle 14, with a second coil spring 58 extending linearly on a rear side of the button 52 in embedded fashion within said second handle.

According to this configuration, and upon the button 52 being inwardly depressed in the direction of arrow 60, a clearance is established between the internally configured slot 54 and the stem 56. At this point, a pulling or withdrawing force exerted by the coil spring 58 on the elongated stem 56, see arrow 62, with an opposite forward end 64 of the stem 56 being retracted from an engaging location with a downwardly angled abutment location of the tab 48.

It is noted that the spring 58 in the position of FIG. 4 is tensioned such that its bias is to pull the stem 56 along the direction of arrow 62. Releasing of the tab 48 from the forward edge abutment 64 of the stem 56 results in the coil spring 42 exerting a downward pivoting force causing the washer 32 to rotate about the hub 36 with the scoop 30 being caused to pivot upwardly as shown in FIG. 4. The construction of the button 52 is further such that it can be reset in order to reverse engage the stem 64 (in a direction opposite to arrow 62) to the tab 48.

Having described my invention, other and additional preferred embodiments will become apparent to those skilled in the art to which it pertains, and without deviating from the scope of the appended claims.

We claim:

1. A rongeur type bone removal device, comprising:
   first and second pivotally secured handles contoured along rear extending grasping portions, each of said handles including a forward circular and overlapping portion;
   said first handle terminating forwardly of its overlapping portion in an integrally formed upper jaw exhibiting an elongated depth defining and downwardly open profile integrating a continuous plurality of alligator type gnawing teeth;
   said second handle terminating forwardly of its overlapping portion in an upwardly open facing and depth defining lower jaw aligning with said teeth of said upper jaw, said lower jaw exhibiting an upper continuous blade edge which matches said profile of said downwardly facing teeth so that that, upon positioning said jaws on opposite sides of a section of bone to be removed, inward opposing compression applied to said handles results in said jaws pivoting together about a pivotally connecting hub said overlapping portions so that said teeth abut said continuous blade edge concurrent with a volume of bone being excised and deposited within an interior chamber defined in said lower jaw;
   a trigger ejection mechanism for assisting in ejection of previously deposited bone and like debris from within said lower jaw interior collection chamber; said ejection mechanism further including an elongated scoop extending from a washer shaped portion mounted upon said hub, such that said scoop is supported within said lower chamber in a first position, a finger projecting from said washer shaped portion between said handles and, in said first position, being latched to an underside of said second handle, and a release button integrated into said second handle with a stem extending between said button and engaging an upper tab formed with said finger in said first position; and
   upon depressing said button, said stem being caused to displace out of contact with said tab, resulting in a spring bias exerting upon said finger to rotate said washer shaped portion and said elongated scoop to a second upwardly pivoted position in which said scoop upwardly ejects the debris from within said chamber.

2. The device as described in claim 1, said spring bias further comprising a coil spring seating within an inner elongated and recessed profile defined in depth extending fashion from an underside accessible location of said second handle proximate said overlapping circular portions of said jaws, with a base mounting location of said spring engaging said finger projection at a location offset from its pivot fulcrum provided by said coaxial hub.

3. The device as described in claim 2, further comprising said tab extending upwardly from a rearward proximate end of said finger, rearwardly of said coil spring, and seating within a mating recess profile defined in a rearwardly spaced and downwardly communicating location of said upper handle which is proximate to said inner seating location of said coil spring, said release button further including a spring biased push button mounted at a rearward location of said upper handle and exhibiting an inner slot in communication with said elongated stem embedded within an elongated recess defined in said second handle, a second coil spring extending linearly on a rear side of said button in embedded fashion within said second handle, upon said button being inwardly depressed, a clearance being established between said internally configured slot and said stem, a pulling force exerted by said coil spring on said elongated stem resulting in an opposite forward end of said stem being retracted from an engaging location with a downwardly angled abutment location of said tab.

\* \* \* \* \*